(12) United States Patent
Wodicka et al.

(10) Patent No.: US 6,705,319 B1
(45) Date of Patent: Mar. 16, 2004

(54) MINIATURE ACOUSTICAL GUIDANCE AND MONITORING SYSTEM FOR TUBE OR CATHETER PLACEMENT

(75) Inventors: George R. Wodicka, West Lafayette, IN (US); Eduardo J. Juan, San Juan, PR (US); Jeffrey P. Mansfield, Cambridge, MA (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/580,817

(22) Filed: May 26, 2000

(51) Int. Cl.⁷ .............................................. A61M 16/00
(52) U.S. Cl. ............................ 128/207.14; 128/200.26; 181/22
(58) Field of Search .................. 128/207.14, 207.15, 128/200.26; 181/22

(56) References Cited

U.S. PATENT DOCUMENTS

| | | | |
|---|---|---|---|
| 4,326,416 A | * 4/1982 | Fredberg | 600/533 |
| 4,344,436 A | * 8/1982 | Kubota | 604/264 |
| 4,431,005 A | * 2/1984 | McCormick | 600/433 |
| 4,445,501 A | * 5/1984 | Bresler | 600/12 |
| 4,449,522 A | * 5/1984 | Baum | 128/200.26 |
| 4,840,172 A | * 6/1989 | Augustine et al. | 128/207.14 |
| 4,943,770 A | * 7/1990 | Ashley-Rollman et al. | 342/207.17 |
| 5,056,514 A | * 10/1991 | DuPont | 128/207.14 |
| 5,331,967 A | * 7/1994 | Akerson | 600/529 |
| 5,445,144 A | 8/1995 | Wodicka et al. | |
| 5,563,848 A | * 10/1996 | Rogers et al. | 367/99 |
| 5,641,892 A | * 6/1997 | Larkins et al. | 73/19.03 |
| 5,666,960 A | 9/1997 | Fredberg et al. | |
| 5,746,699 A | 5/1998 | Fredberg et al. | |
| 5,752,921 A | * 5/1998 | Orr | 600/533 |
| 5,823,965 A | 10/1998 | Rasmussen | |
| 5,848,973 A | 12/1998 | Lane | |
| 5,868,682 A | 2/1999 | Combs et al. | |
| 5,882,314 A | 3/1999 | Fredberg et al. | |
| 5,902,237 A | 5/1999 | Glass | |
| 6,139,504 A | 10/2000 | Lane | |
| 6,161,537 A | * 12/2000 | Gravenstein et al. | 128/200.26 |
| 6,164,277 A | * 12/2000 | Merideth | 128/207.14 |
| 6,183,423 B1 | 2/2001 | Gaumond et al. | |
| 6,349,720 B1 | * 2/2002 | Clark | 128/200.26 |

OTHER PUBLICATIONS

P.K. Birmingham, F. W. Cheney, and R. J. Ward, "Esophageal Intubation: A Review of Detection Techniques," *Anesthesia and Analgesia*, vol. 65, pp. 886–891, 1986.

B.S. Turner, "Maintaining the Artificial Airway: Current Concepts," *Pediatric Nursing*, vol. 16, pp. 487–493, 1990.

J.P. Mansfield and G. R. Wodicka, "Using Acoustic Reflectometry to Determine Breathing Tube Position and Patency," *Journal of Sound and Vibration*, vol. 188, pp. 167–188, 1995.

(List continued on next page.)

*Primary Examiner*—Aaron J. Lewis
*Assistant Examiner*—Mital Patel
(74) *Attorney, Agent, or Firm*—Barnes & Thornburg

(57) ABSTRACT

An apparatus and method are disclosed for acoustically guiding a distal end of a tube within a body. An incident sound pulse is generated and propagated down the tube into the body. A plurality of microphones are located in the tube and are positioned to detect pulses traveling through the tube. A discriminator distinguishes between incident sound pulses and those that are reflected from within the body. The detected sound pulses are processed to provide an indication of the location of the distal end of the tube within the body, to assist with the guidance of the insertion into the body, to estimate dimensions of the body adjacent the distal end of the tube, and to determine if the tube is obstructed.

32 Claims, 9 Drawing Sheets

OTHER PUBLICATIONS

J.P. Mansfield, D.C. Shannon, and G. R. Wodicka, "Acoustic Method to Quantitatively Assess the Position and Patency of Infant Endotracheal Tubes: Preliminary Reults in Rabbits," *Pediatric Pulmonology*, vol. 26, pp. 354–361, 1998.

J. Ware and K. Aki, "Continuous and Discrete Inverse–Scattering Problems in a Stratified Elastic Medium," *Journal of the Acoustical Society of America*, vol. 45, pp. 911–921, 1968.

J. L. Flannagan, "Speech Analysis Synthesis and Perception," Second Edition ed. New Jersey: Springer–Verlag, 1972, pp. 24–35, 52–53.

I. Marshall, "Acoustic Reflectometry with an Arbitrarily Short Source Tube," *Journal of the Acoustical Society of America*, vol. 91, pp. 3558–3564, 1992.

M. R. Schroeder, "Determination of the Geometry of the Human Vocal Tract by Acoustic Measurements," *Journal of the Acoustical Society of America*, vol. 41, pp. 1002–1010, 1967.

B. Louis, G. Glass, B. Kresen, and J. Fredberg, "Airway Area by Acoustic Reflection: The Two–Microphone Method," *Journal of Biomechanical Engineering*, vol. 115, pp. 278–285, 1993.

B. Louis, G. M. Glass, and J. J. Fredberg, "Pulmonary Airway Area by the Two–Microphone Acoustic Reflection Method," *Journal of Applied Physiology*, vol. 76, pp. 2234–2240, 1994.

I. Marshall, "The Production of Acoustic Impulses in Air," *Meas. Sci. Technology*, pp. 413–418, 1990.

* cited by examiner

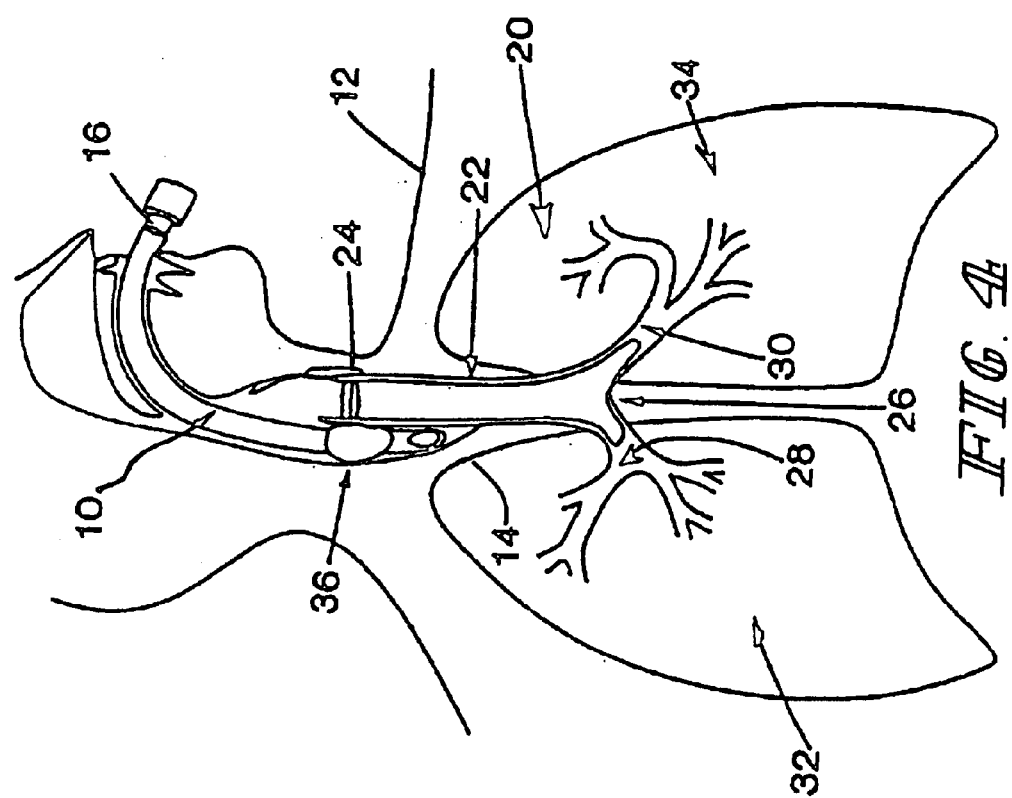
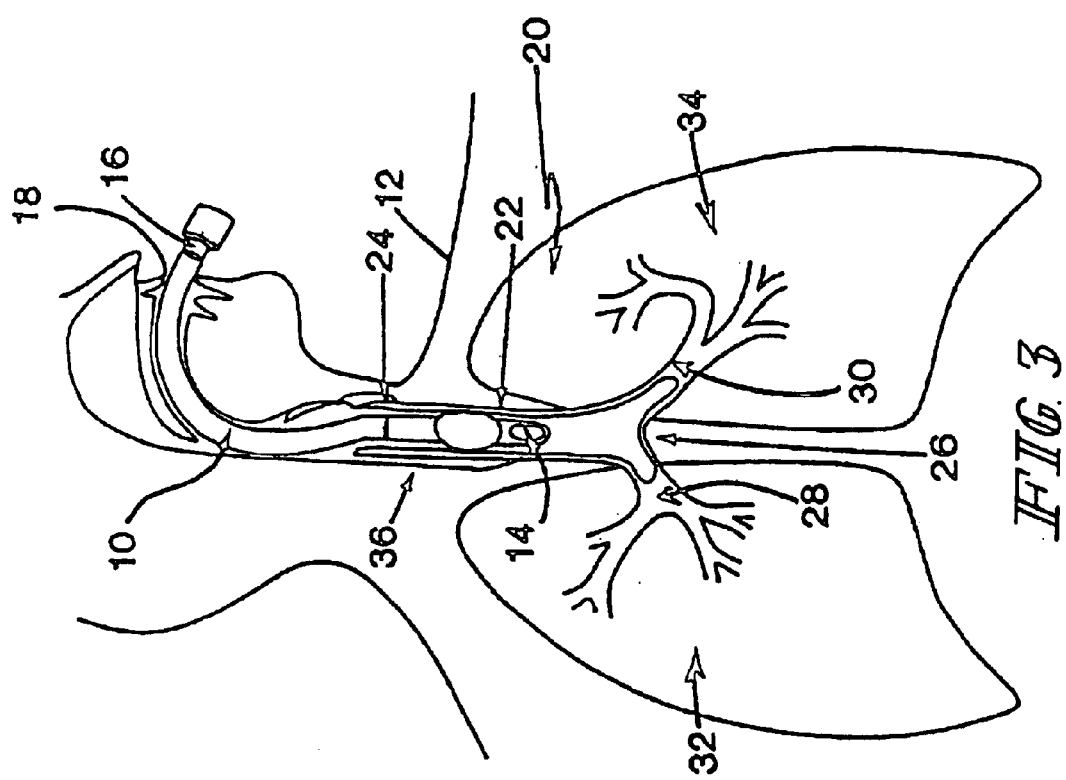

MINIATURE ACOUSTICAL GUIDANCE AND MONITORING SYSTEM FOR TUBE OR CATHETER PLACEMENT

Government Rights

Research relating to this invention was supported in part by the U.S. Government under Grant No. 500 1285 2418 awarded from the National Science Foundation. The U.S. Government may have certain rights in this invention.

BACKGROUND AND SUMMARY OF THE INVENTION

The present invention relates to an apparatus and method for acoustically guiding, positioning, and monitoring a tube or catheter within a body. More particularly, the present invention relates to an apparatus and method to guide the placement of a tube in a body conduit or cavity, to monitor the position of the tube, and to insure the patency of the tube in the body using a noninvasive acoustic technique.

Endotracheal tubes (hereinafter "ETTs"), often referred to as breathing tubes, are used to provide a conduit for mechanical ventilation of patients with respiratory or related problems. An ETT is inserted through the mouth or nose and into the trachea of a patient for several reasons: (1) to establish and maintain an open airway; (2) to permit positive pressure ventilation which cannot be done effectively by mask for more than brief periods; (3) to seal off the digestive tract from the trachea thereby preventing inspiration of forced air into the stomach; and (4) as an anesthesia delivery system.

ETTs are used extensively in the field, emergency rooms, surgical suites, and intensive care units for patients that require ventilatory assistance. During intubation, an ETT is typically inserted into the mouth, past the vocal cords, and into the trachea. The proper location of the ETT tip is roughly in the mid-trachea. However, there are at least three possible undesired placement positions that can result, either during intubation or due to a subsequent dislodgment. One of these positions is in the esophagus. Another undesired position occurs from over-advancement of the ETT past the bifurcation of the trachea (carina) and into one of the mainstem bronchi. A third is above the vocal cords in the vocal tract.

The structure of the human airways is extremely complex. At the upper end of the trachea is the larynx containing the vocal folds, and at the lower end is the first bifurcation, known as the carina. The adult trachea is approximately 1.4 to 1.6 cm in diameter and 9 to 15 cm long. The newborn trachea averages about 0.5 cm in diameter and 4 cm in length. The airways that are formed by the carina are the right primary bronchus and the left primary bronchus. The right primary bronchus is shorter, wider, and more vertical than the left primary bronchus. For this reason a majority of erroneous ETT insertions past the carina tend to follow the right primary bronchus. Continuing farther down the airways, the bronchi branch into smaller and smaller tubes. They finally terminate into alveoli, small airfilled sacs where oxygen-carbon dioxide gas exchange takes place.

Providing a correctly positioned and unobstructed endotracheal tube is a major clinical concern. Any misplacement or obstruction of an ETT can pose a threat to the patient's health. Misdirecting the ETT into the esophagus or locating the tip where there is a significant obstruction of its lumen can result in poor ventilation of the patient and eventually lead to cardiac arrest, brain damage or even death. Further, if the ETT is misplaced into a mainstem bronchus, lung rupture can occur.

If an ETT is obstructed with secretions or debris, a procedure known as endotracheal suctioning must be performed to clear the ETT. This procedure consists of introducing a sterile catheter through the ETT into the trachea, and applying negative pressure as the catheter is withdrawn. It has been estimated that this procedure is performed in Neonatal Intensive Care Units around 22,000 times per day in the U.S., and in many cases, it is performed as a preventive measure. Even though this procedure is performed very frequently, there are infrequent complications associated with its practice. These complications include hypoxia, bradycardia, tissue trauma, increase intracranial pressure, and tracheal or pharyngeal perforation.

In an attempt to avoid possible complications with ETT use, several techniques have been developed to aid clinicians in the proper placement/location of ETTs. Guidelines for the ideal technique are as follows: (1) the technique should work as well for difficult intubations as it does for those not so difficult; (2) the technique should indicate a proper ETT tip location unequivocally; (3) esophageal intubation must always be detected; and (4) clinicians must understand the technique and how to use it. The known techniques for clinical evaluation of ETT location include direct visualization of the ETT placement, chest radiography, observation of symmetric chest movements, auscultation of breath sounds, reservoir bag compliance, the use of a video stethoscope, fiberoptic bronchoscopy, pulse oximetry, and capnometry. However, none of the listed techniques allow a health care provider to constantly monitor the precise location of an ETT within the trachea, or the degree of obstruction of its lumen.

Apparatuses and methods for acoustically guiding, positioning, and monitoring tubes within a body are known in the art. See, for example, U.S. Pat. No. 5,445,144 to Wodicka et al., incorporated herein by reference, which discloses an apparatus and method for acoustically monitoring the position of a tube within a body conduit. In a preferred embodiment, a sound pulse is introduced into a wave guide and is recorded as it passes by a microphone located in the wave guide wall. After propagating down the ETT, the sound pulse is emitted through the distal tip of the ETT into the airway (or wherever in the body the tip of the ETT is located) and an acoustic reflection propagates back up to the wave guide for measurement by the same microphone. An absorptive material is located at the end of the wave guide to prevent further reflections of the sound pulse. The amplitude and the polarity of the incident and reflected sound pulse are used to estimate the characteristics of the airway at the tip of the ETT, and thereby guide the ETT placement or monitor the ETT for patency. In one preferred embodiment, a valve movable between a first and second position was included to provide communication between a mechanical ventilator and the proximal end of the ETT in the first position, and to provide communication between the wave guide and the proximal end of the ETT in the second position. Therefore, it is necessary during acoustical monitoring operations using the Wodicka et al. device to temporarily disconnect the mechanical ventilator (by switching valve positions) from the ETT.

As disclosed by Wodicka, et al., the acoustical properties of the airways of a respiratory system change dramatically over the audible frequency range. At very low frequencies, the large airway walls are yielding and significant wall motion occurs in response to intra-airway sound. In this frequency range, the airways cannot be represented accurately as rigid conduits and their overall response to sonic pulses is predictably complex. At very high audible frequencies, the large airway walls are effectively more rigid due to their inherent mass. However, one-dimensional sound propagation down each airway segment cannot be ensured as the sonic wavelengths approach in size the diameter of the segment, and effects of airway branching are thought to increase in importance. There appears to be a finite range of frequencies between roughly 500 and 6,000 Hz where the large airways behave as nearly rigid conduits and the acoustical effects of the individual branching segments are not dominant. It is over this limited frequency range where the complicated branching network can be approximately represented as a flanged "horn" and where its composite acoustical properties reflect the total cross-sectional area of the airways.

The method and apparatus of the present invention distinguish between esophageal, tracheal, and bronchial intubations; are sensitive to small movements of the ETT; are able to continuously monitor the position of the distal tip of the ETT; and are not invasive. Furthermore, the apparatus of the present invention has no moving parts, and can be easily understood and operated by skilled clinicians.

According to one aspect of the present invention, an apparatus is provided for acoustically detecting the location of a distal end of a tube relative to a body conduit into which the tube is being inserted. The tube has a proximal end, and a distal end formed for insertion into the body conduit. The apparatus includes a speaker for generating a sound pulse in the tube; a first microphone for detecting a sound pulse in the tube at a distal position relative to the speaker, and for generating a first signal corresponding to the detected sound pulse; a second microphone for detecting a sound pulse at a position in the tube between the first microphone and the speaker, and for generating a second signal corresponding to a detected sound pulse; and a processor configured to receive the first and second signals and to discriminate between a distally traveling sound pulse and a proximally traveling sound pulse, the processor using the first or second signal generated from detection of the proximally traveling sound pulse to determine and report the location of the distal end of the tube relative to the body conduit.

In one embodiment of the invention, the processor is further configured to detect either a total or partial blockage in the tube. The processor can also be configured to detect a kink in the tube.

In another embodiment of the invention, the processor provides a signal representing the dimensions of the body conduit adjacent the distal end of the tube. In this embodiment, the invention can further include a warning signal generator for signaling when the dimensions signaled by the processor are not within a predetermined range. Furthermore, the warning signal generator can signal when the distal end of the tube moves relative to the body conduit.

In one embodiment of the invention, the tube is adapted to be coupled to a medical device, such as a mechanical ventilator, a breathing bag, an anesthesia machine, or an infusion pump. In a further embodiment, a display can be provided in electronic communication with the processor. The display can be designed to provide an indication of the dimensions of the body conduit adjacent the distal end of the tube, an indication of the patency of the tube, or an indication of the location of the distal end of the tube relative to the body conduit.

In another embodiment of the invention, there is provided an apparatus for acoustically detecting the location of a distal end of a tube relative to a body into which the tube is being inserted. The apparatus includes a sound pulse generator, a sound pulse receiver for signaling the detection of a sound pulse, a position indicator configured to report the location of the distal end of the tube relative to the body using the signal from the sound pulse receiver, and means for discriminating between a sound pulse traveling away from the distal end of the tube and a sound pulse traveling toward the distal end of the tube. In this embodiment, the sound pulse receiver is, for example, a first microphone and a second microphone, or a directionally sensitive microphone. The sound pulse receiver can be located at a distal position relative to the sound pulse generator, or at a proximal location relative to the sound pulse generator. In one aspect of this embodiment, the position indicator can also report whether the tube is obstructed. In another aspect, the position indicator provides an estimate of dimensions of the body adjacent the distal end of the tube. In yet another aspect, a warning signal generator is provided for signaling when the dimensions estimated by the position indicator are not within a predetermined range. The warning signal generator can be further configured to signal when the distal end of the tube moves relative to the body.

In yet another embodiment of the invention, a method of acoustically detecting the location of a distal end of a tube relative to a body is provided. The method includes the steps of generating a sound pulse in the tube; detecting a sound pulse; determining the direction of travel of the detected sound pulse; and determining the position of the distal end of the tube relative to the body using the detected sound pulse when the detected sound pulse is determined to be traveling away from the distal end of the tube. In one aspect of this embodiment, the method further includes the step of determining whether the tube is obstructed. In another aspect, the invention further includes the step of determining whether the tube is kinked. In yet another aspect of this method, the position determining step can include estimating the dimensions of the body adjacent the distal end of the tube. The position determining step can include the step of comparing a first signal representing a sound pulse detected by a first microphone with a second signal representing a sound pulse detected by a second microphone.

In a further embodiment of the invention, an apparatus for acoustically detecting the location of a distal end of a gas or liquid filled tube within a body conduit includes a sound pulse generator coupled to the tube, a sound pulse receiver or receivers coupled to the tube at a distal position relative to the sound pulse generator, a position indicator configured to report the location of the distal end of the tube in the body conduit using signals from the sound pulse receiver or receivers, and means for differentiating between a sound pulse traveling away from the distal end of the tube and a sound pulse traveling toward the distal end of the tube.

Additional objects, features, and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

The detailed description particularly refers to the accompanying figures in which:

FIG. 3 is a diagrammatical view illustrating proper insertion of an endotracheal tube (ETT) into a trachea of a human body;

FIG. 4 is a diagrammatical view illustrating improper placement of the ETT into an esophagus;

DETAILED DESCRIPTION OF THE DRAWINGS

Figure 1:
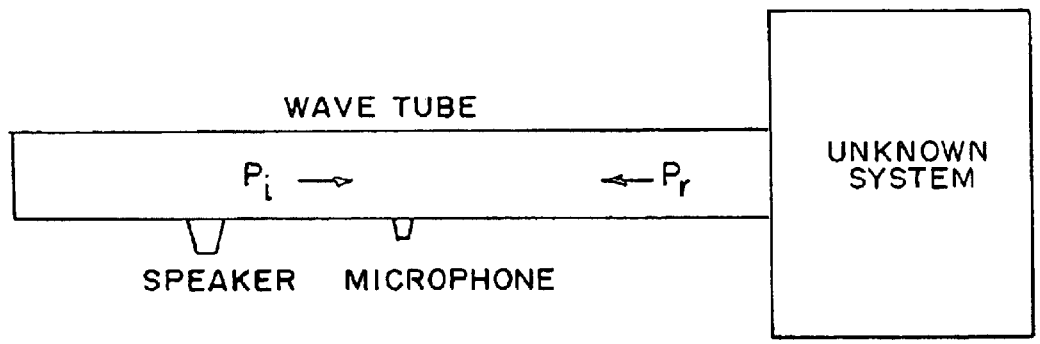
FIG. 1 is a diagrammatical view of a prior art system for determining characteristics of an unknown system.

When it is desired to direct an object (such as a tube, catheter, or medical device) into an unknown system, it is known to generate a sound pulse within the tube or medical device and to receive the reflections of the pulse as they return from the unknown system, similar to the process used in sonar imaging. In the case of a system as shown in FIG. 1, a speaker transmits an incident sound pulse, $P_i$, that travels toward the unknown system. As the incident sound pulse, $P_i$, enters the unknown system, a sound pulse is reflected back, $P_r$, which can be received by the microphone. The reflected sound pulse, $P_r$, can be analyzed to determine various qualities of the unknown system, including the cross sectional area of the system. Furthermore, as the incident sound pulse $P_i$ continues to propagate through the unknown system, additional reflections may occur. These subsequent reflected sound pulses can indicate additional qualities of the unknown system, such as the depth of the system, and whether the cross sectional area changes at all throughout that depth.

Figure 2:
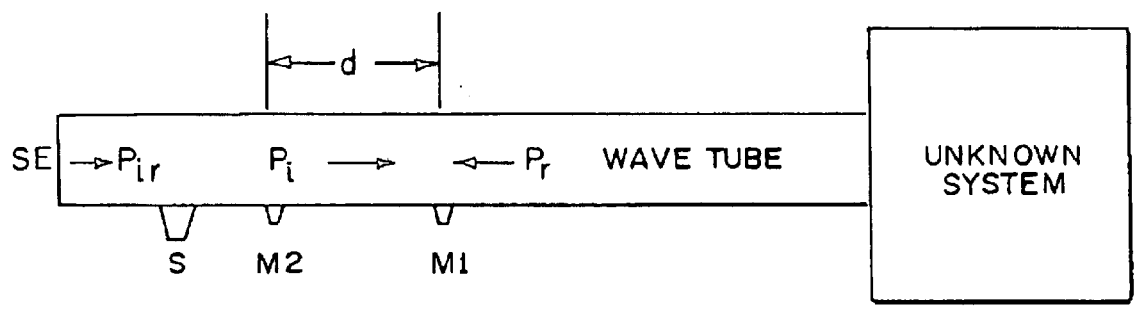
FIG. 2 is a diagrammatical view of a two-microphone system for determining characteristics of an unknown system.

A two-microphone system is shown in FIG. 2, where the two microphones are separated by a distance d. In the two-microphone system, determination can be made as to the direction of travel of a sound pulse, $P_i$ or $P_r$, by analyzing the difference between the instant in which the sound pulse is detected by the first microphone M1, and the instant in which the sound pulse is detected by the second microphone, M2. For example, if a sound pulse is first detected by M1 and then by M2, the pulse is determined to be traveling away from the unknown system, and is thus a reflected pulse $P_r$. In contrast, if a sound pulse is first detected by M2 and then M1, the pulse is determined to be traveling toward the unknown system.

The directional determination of the traveling sound pulse prevents the misreading of sound pulses that are reflected from the speaker end, SE, of the tube, such as $P_{ir}$. For various reasons, an incident sound pulse, $P_i$, may be reflected from the speaker end, SE, of the tube, including the presence of a blockage in the tube, a wall at the end of the tube, or the attachment of another device (i.e. a mechanical ventilator) to the end of the tube. False readings can occur when reflected sound pulse, $P_{ir}$, travels past a single microphone, such as that shown in FIG. 1. However, when two microphones are used, such as in the system illustrated in FIG. 2, a determination of the direction of travel of the reflected sound pulse, $P_{ir}$, can eliminate the possibility of a misreading.

Although the method and apparatus described below relate to guiding and positioning an endotracheal tube (ETT) within a respiratory system of a body, it should be understood that the present invention may be used to guide insertion of gas or liquid filled tubes or catheters into other body conduits or cavities, or in various mechanical operations.

As mentioned above, a method and apparatus for guiding the positioning of an ETT is known in the art. A summary of the theory and analysis associated with determining the position of an ETT follows. For a description of a single microphone system for guiding the insertion of the ETT, and a more detailed description of the analysis and theory involved in determining the position of the ETT, reference can be made to U.S. Pat. No. 5,455,144 to Wodicka, et al., previously incorporated by reference.

Figure 5:
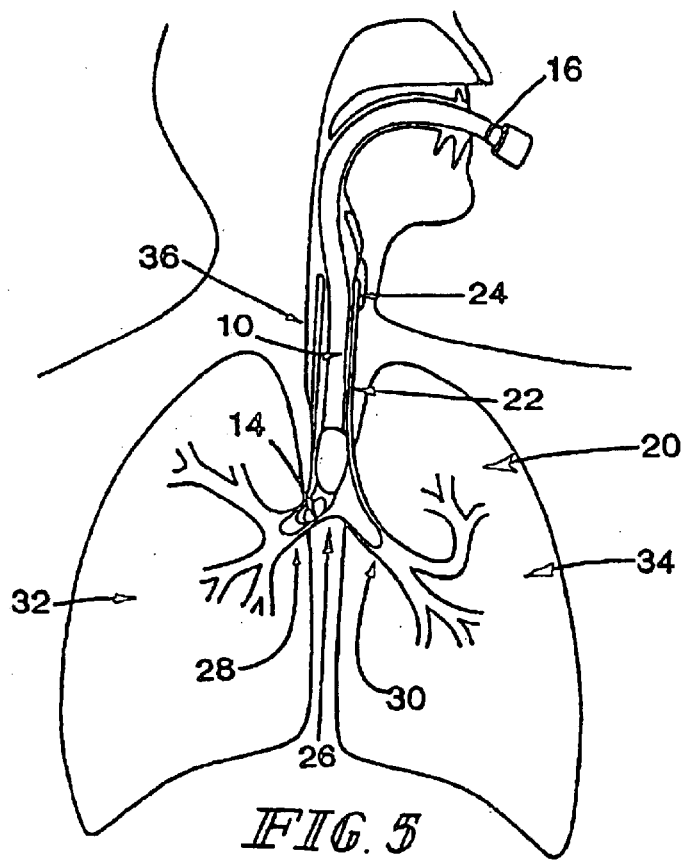
FIG. 5 is a diagrammatical view illustrating improper placement of an ETT past a carina and into a right main bronchus.

Referring now to the drawings, FIGS. 3–5 illustrate insertion of an ETT 10 into a human body 12. ETT 10 includes a hollow tube having a distal end 14 for insertion into body 12 and a connector 16 located outside body 12. Illustratively, ETT 10 is inserted into a mouth 18 of the patient. A respiratory system 20 includes a trachea 22 which extends between vocal folds 24 of a larynx and a first bifurcation known as a carina 26. Airways formed by carina 26 include a right primary bronchus 28 and a left primary bronchus 30. Continuing further down the airway, bronchial tubes branch into smaller and smaller tubes.

FIG. 3 illustrates proper insertion of ETT 10 into trachea 22 between vocal folds 24 and carina 26. For proper mechanical ventilation of the patient, it is important that distal end 14 of ETT 10 is positioned properly within trachea 22 between vocal folds 24 and carina 26 to provide adequate ventilation to both lungs 32 and 34. Insertion of ETT 10 into the trachea 22 is sometimes a difficult procedure. As illustrated in FIG. 4, it is possible for distal end 14 of ETT 10 to miss the entrance to trachea 22 and enter an esophagus 36 leading to the stomach (not shown). Improper placement of ETT 10 into the esophagus is most evident in an emergency room setting which is characterized by high stress and limited time. Improper placement of open distal end 14 of ETT 10 into the esophagus 36 prevents ventilation of lungs 32 and 34.

Improper insertion of distal end 14 of ETT 10 past carina 26 will result in ventilation of only right lung 32 or left lung 34. FIG. 5 illustrates improper insertion of distal end 14 of ETT 10 past carina 26 and into right main bronchus 28. Because right primary bronchus 28 is shorter, wider, and more vertical than left primary bronchus 30, the majority of ETT insertions past carina 26 tend to follow the right primary bronchus 28. One object of the present invention is to detect if ETT 10 is improperly inserted into esophagus 36, right primary bronchus 28, or left primary bronchus 30 and alert a user to the improper placement. The apparatus can then be used to guide movement of ETT 10 back into its proper position within trachea 22.

The complex acoustical properties of the airways are determined by their wall properties, branching structure, and cross-sectional area. At the low frequencies associated with breathing, the large airway walls exhibit elastic behavior and alter airway size in response to pressure changes. At higher acoustical frequencies, their behavior is effectively more rigid due to inherent wall mass. The frequency range over which the transition to nearly rigid tube behavior is not known, but for example, modeling and experimental efforts suggest that the trachea approaches rigidity at frequencies near 500 Hz. In contrast to wall properties, the effect of branching on the overall acoustical properties has been hypothesized to be most significant at frequencies above 6,000 Hz as the sonic wavelengths begin to approach airway dimensions. Also, as the sound wavelengths approach airway dimensions with increasing frequency, one-dimensional acoustic wave propagation down the airways cannot be assured as other cross modes of propagation can occur and thereby significantly increase the acoustical complexity of the response.

Thus, there is a band of frequencies between about 500 Hz and about 6,000 Hz over which the acoustical response of the large airways is strongly affected by the cross-sectional area and relatively less affected by wall properties and branching. Over this range it has also been indirectly shown that acoustical losses due to viscous and thermal effects are small. This dictates that plane wave propagation in the large airways at these frequencies would occur at nearly free field speeds as if the airways were rigid conduits. For this mode of propagation, reflections of a sonic pulse occur spatially at points of changes in acoustic impedance Z, which equals the characteristic acoustic impedance, $Z_0$:

$$Z = Z_0 = \frac{\rho_0 c}{A} \frac{dyne \cdot s}{cm^5} \quad (1)$$

where $\rho_0$=density of air in g/cm$^3$, c is the sound speed in cm/s as determined by the density and stiffness of air, and A is the cross-sectional area of the tube in cm$^2$. Thus, for a non-changing propagation medium such as air, Z is predicted to be only a strong function of the cross-sectional area of the tube or airways at frequencies between about 500 Hz and about 6,000 Hz.

Figure 6:
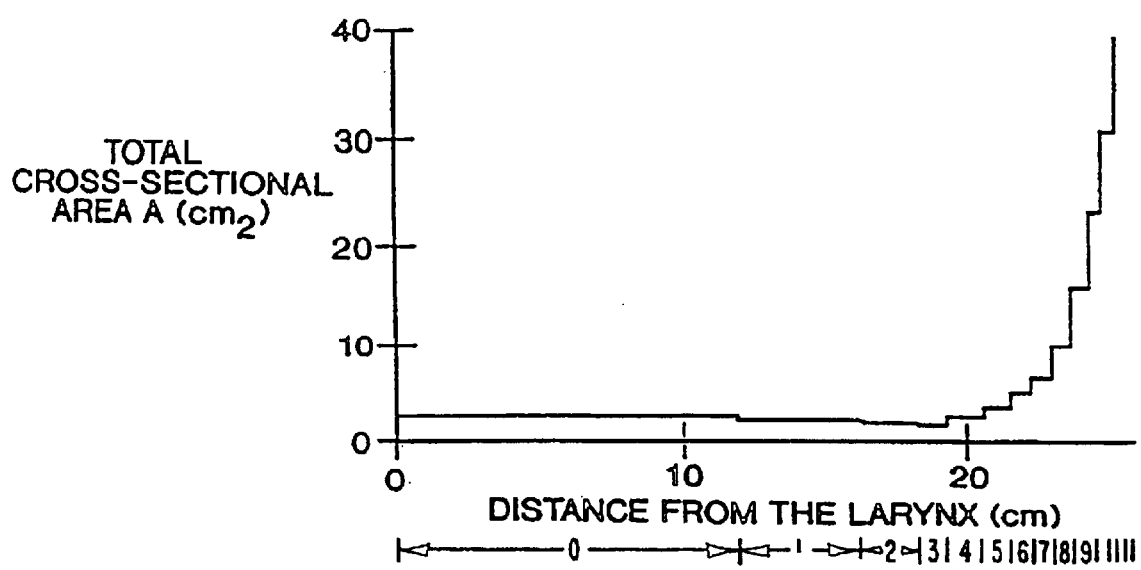
FIG. 6 is a graph representing a total cross sectional area of the airways of a respiratory system versus distance from vocal folds within a larynx.

If one approximates the total cross-sectional area A of the branching airways as a function of the distance below vocal folds 24 as illustrated graphically in FIG. 6, an interesting feature becomes evident. Namely, A is nearly constant for the first few airway branching levels and then increases very rapidly thereafter. This geometrical approximation suggests that from an acoustical perspective, the airways of respiratory system 20 behave in a similar manner to a rapidly flanged "horn" or "trumpet" that is open to a nearly zero-pressure boundary condition at its terminal end.

Figure 7:
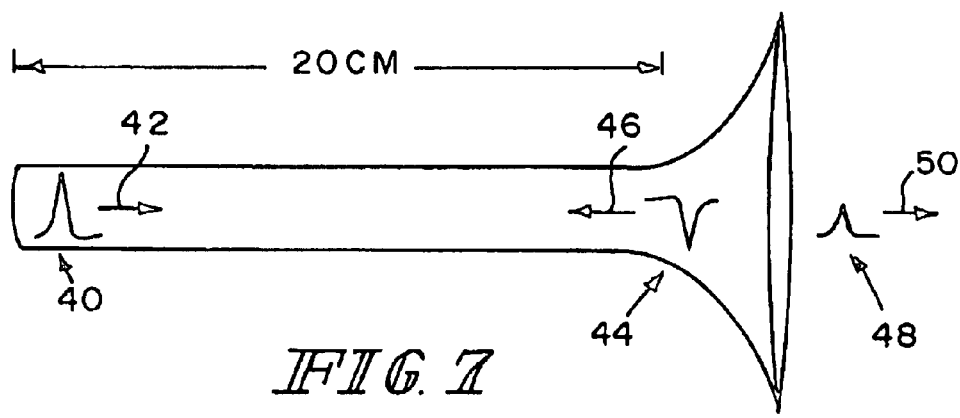
FIG. 7 is a diagrammatical illustration of a simple acoustical flanged "horn" model which represents the acoustical properties of the airway of the respiratory system.

The response of this simple model of the airways to a sound pulse with energy between 500 Hz and 6,000 Hz is depicted in FIG. 7. The incident pulse 40 travels in the direction of arrow 42 in the model without significant reflection for a distance of roughly 20 cm since there is little change in A. When the incident pulse 40 encounters the flared region of the model, a portion 44 of the sonic energy is reflected back up the airways in the direction of arrow 46, and a portion 48 is transmitted further into the branching structure in the direction of arrow 50. Since the flange is quite rapid due to the large spatial rate of change of A, a significant portion of the incident energy is reflected at this "acoustical end" of the airways.

For a plane wave that is incident upon a boundary between two media with acoustic impedances $Z_0$ and $Z_1$, the amplitude of the reflection can be expressed as a dimensionless reflection coefficient, R, equal to the ratio of reflected $p_r$ to incident $p_i$ acoustic pressure as follows:

$$R = \frac{p_r}{p_i} = \frac{Z_1 - Z_0}{Z_1 + Z_0} \quad (2)$$

In the case of propagation within a rigid tube of changing cross-sectional area A that is entirely filled with air, this relationship for R can be rewritten in terms of only areas via substitution of equation (2):

$$R = \frac{A_0 - A_1}{A_0 + A_1} \quad (3)$$

Noting that for the case of a large increase in area at the boundary ($A_1 >> A_0$), R approaches $-1$ indicating a reflection that approaches the absolute amplitude of the incident pulse but is inverted. Conversely, for the case of a large decrease in area at the boundary ($A_1 << A_0$), R approaches $+1$ and thus the reflection would be expected to approach the amplitude of the incident pulse but not be inverted. If the pressure amplitude of a reflection from a boundary is measured and compared to the incident pressure amplitude, knowledge of the initial area $A_0$ can be used to estimate the area $A_1$ after the boundary, as can be seen by rearranging equation (3):

$$A_1 = \left[\frac{1-R}{1+R}\right] A_0 \text{ cm}^2 \quad (4)$$

Figure 8:
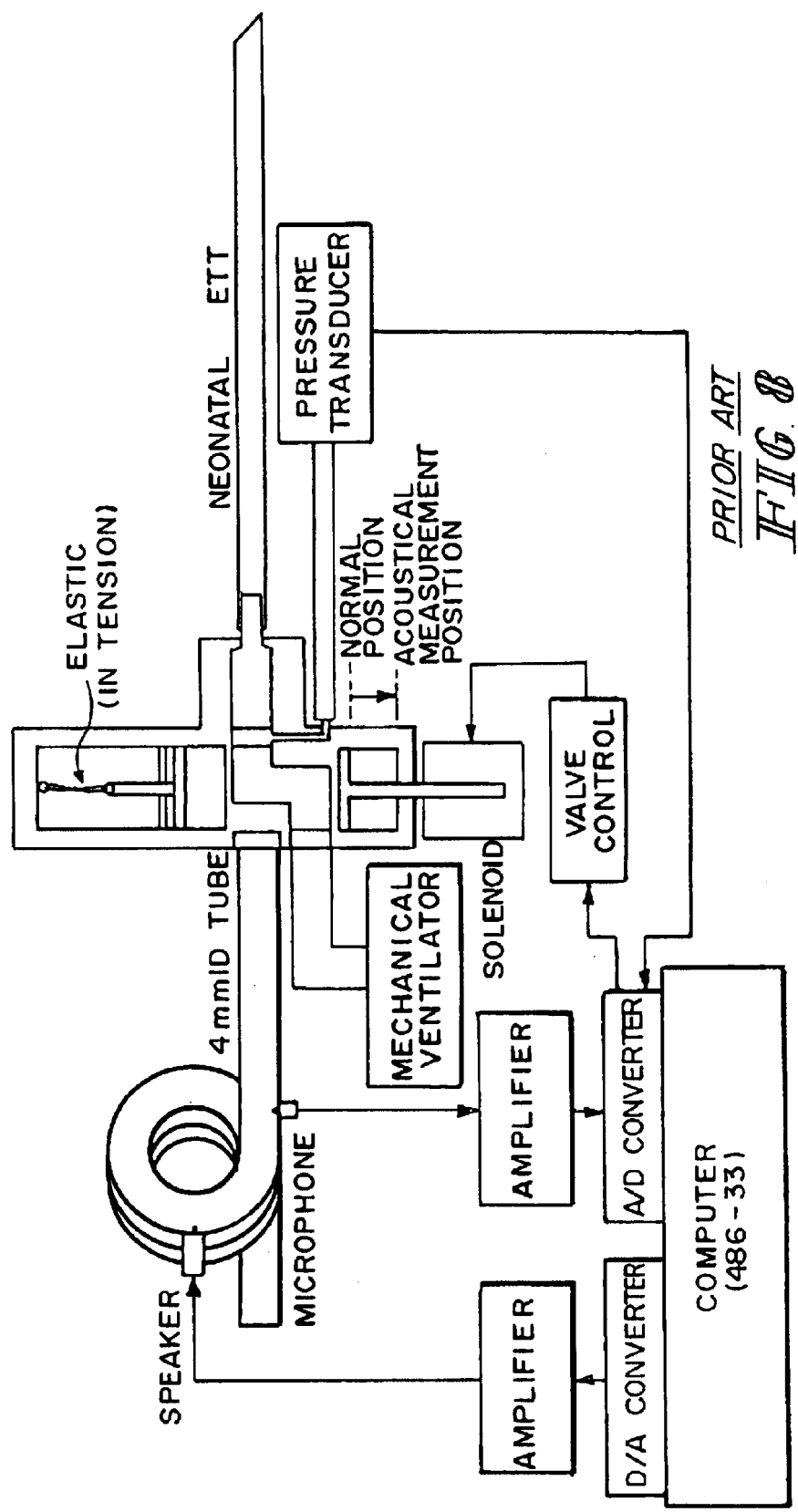
FIG. 8, is a diagrammatical view of a prior art apparatus for guiding a distal end of a tube within a body using a single microphone.

FIG. 8 shows the prior art apparatus disclosed by the Wodicka '144 patent. As shown, a single microphone is used for receiving the sound pulse transmitted by the speaker, and a valve is coupled to the ETT for alternating between a link to the microphone/speaker combination and a link to the mechanical ventilator.

Figure 9:
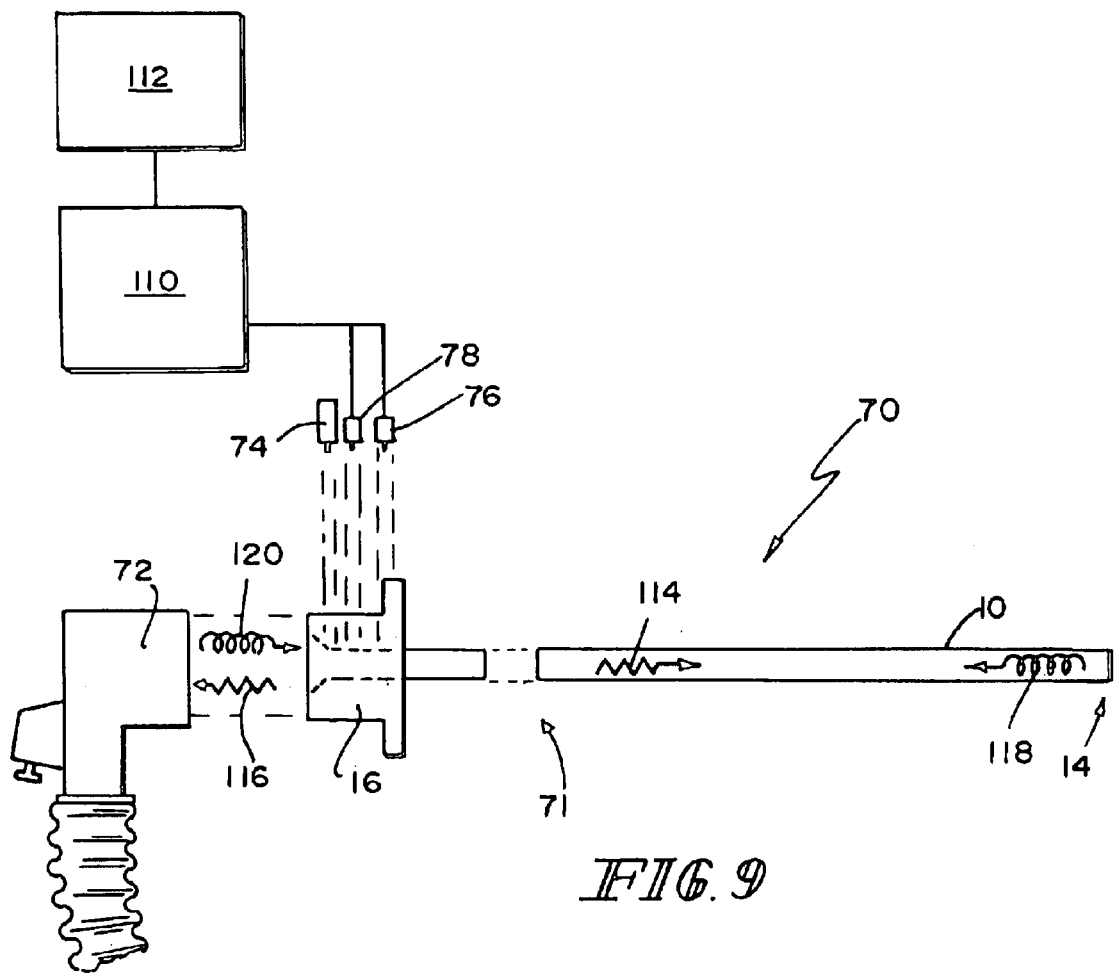
FIG. 9 is a diagrammatical view of one embodiment of the apparatus of the present invention for detecting the location of a distal end of a tube within a body conduit.

FIG. 9 illustrates one embodiment of the apparatus 70 for acoustically guiding and monitoring the position of a tube or catheter (i.e. ETT 10) within a body. For exemplary purposes, an ETT 10 connected to a ventilator 72 is shown in the described embodiment. However, it should be understood that any tube, catheter, or similar device could be substituted for ETT 10, and ventilator 72 could instead comprise a medical device used in combination with the tube, catheter, or similar device. Apparatus 70 includes tube 10 which is defined by a distal end 14 and a proximal end 71, the proximal end 71 being communicatively coupled to any type of medical device (i.e. a mechanical ventilator) 72 that is capable of cooperating with the apparatus 70. Apparatus 70 further includes a connector 16 that connects tube 10 with the medical device 72. In the illustrated embodiment of the invention, a speaker 74 is coupled to the connector 16, a first microphone 76 is coupled to the connector 16 at a distal position relative to speaker 74, and a second microphone 78 is positioned to lie between speaker 74 and microphone 76.

It should be understood that while the disclosed embodiments show first and second microphones 76, 78 positioned distally relative to speaker 74, it is equally possible to position speaker 74 distally from first and second microphones 76, 78 (not shown). In such an embodiment, similar, yet distinct, determinations and calculations can be made to determine the distal position of the tube and its degree of obstruction.

Referring again to the embodiment disclosed in FIG. 9, microphones 76, 78 are in electronic communication with a discriminator 110, wherein signals representative of detected sound pulses are transmitted by microphones 76, 78 and analyzed and compared as discussed further below. Discriminator 110 determines whether a received sound pulse is traveling toward distal end 14 or toward ventilator 72. Discriminator 110 then transmits a signal to a position indicator 112, which uses the signals representative of the detected sound pulses to determine the position of the distal end 14 of the tube 10.

As shown in FIG. 9, speaker 74 generates an incident sound pulse which propagates through connector 16 in two directions: distally as traveling pulse 114, and proximally as traveling pulse 116. Upon the occurrence of distally traveling pulse 114 reaching distal end 14 of tube 10, a reflected pulse 118 is sent back through tube 10 toward microphones 76, 78. Likewise, a reflected pulse 120 can be sent back from ventilator 72 toward microphones 76, 78.

Figure 10:
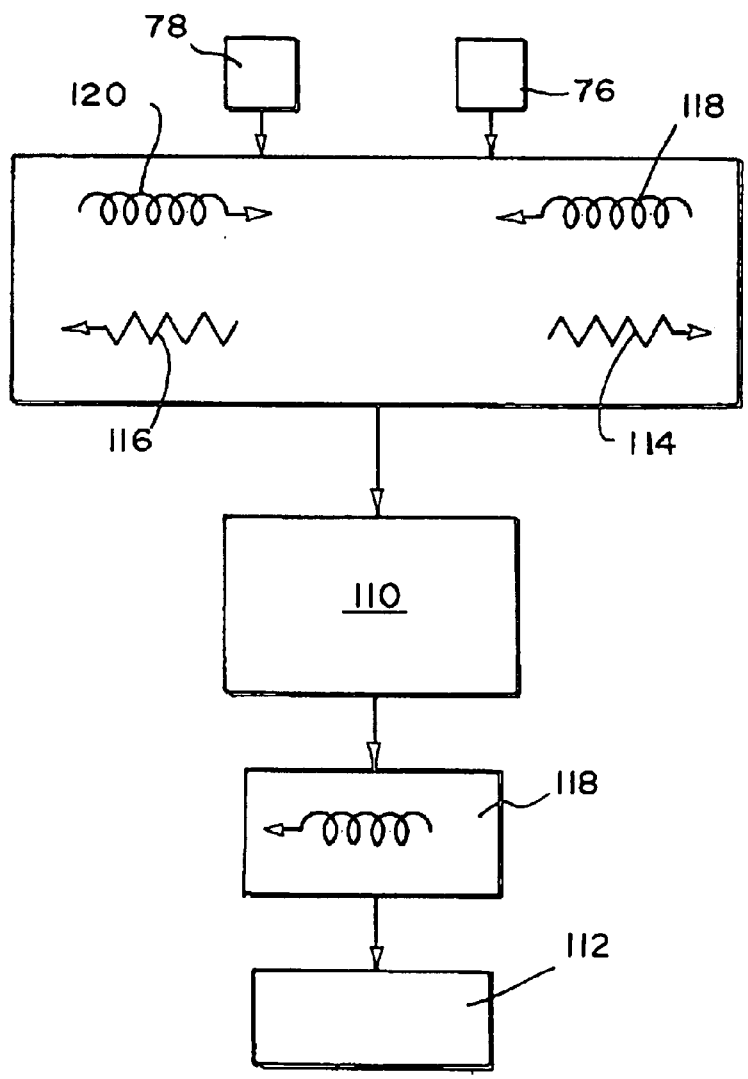
FIG. 10 is a diagrammatical view showing the process utilized by the discriminator of FIG. 9 to select a sound pulse.

As exemplified in FIGS. 9 and 10, microphones 76,78 detecting a distally traveling pulse 114 provide signals to discriminator 110. Thereafter, a reflected pulse 118 returns from distal end 14 of tube 10, the pulse 118 being detected by first microphone 76 and then by second microphone 78 as it travels back toward ventilator 72. Discriminator 110 generates a signal representing the direction of travel of reflected sound pulse 118, and delivers the signal to position indicator 112. In the event a sound pulse 116 is reflected back from ventilator 72 as reflected sound pulse 120, the reflected pulse 120 is detected first by second microphone 78 and then detected by first microphone 76. Microphones 76, 78 deliver signals to discriminator 110, which determines that reflected sound pulse 120 is traveling distally, and identifies that sound pulse 120 is not to be analyzed by position indicator 112 in the determination of the position of distal end 14 of tube 10.

In one embodiment, the time $t_0$ of sound pulse generation by speaker 74 can be noted for later reference. Alternatively, time $t_0$ can be defined as the time of detection of distally traveling pulse 114 by at least one of microphones 76, 78. Time $t_0$ is then compared by position indicator 112 to time $t_1$, which represents the time of detection of a reflected pulse 118. In the case that reflected pulse 118 is a reflection from the bronchi, the difference in time $(t_1-t_0)$ is indicative of the distance between the distal end 14 of tube 10 and the bronchi. The distance is therefore determined by the following equation:

$$d = \frac{c(t_1 - t_0)}{2} \quad (5)$$

Figure 11:
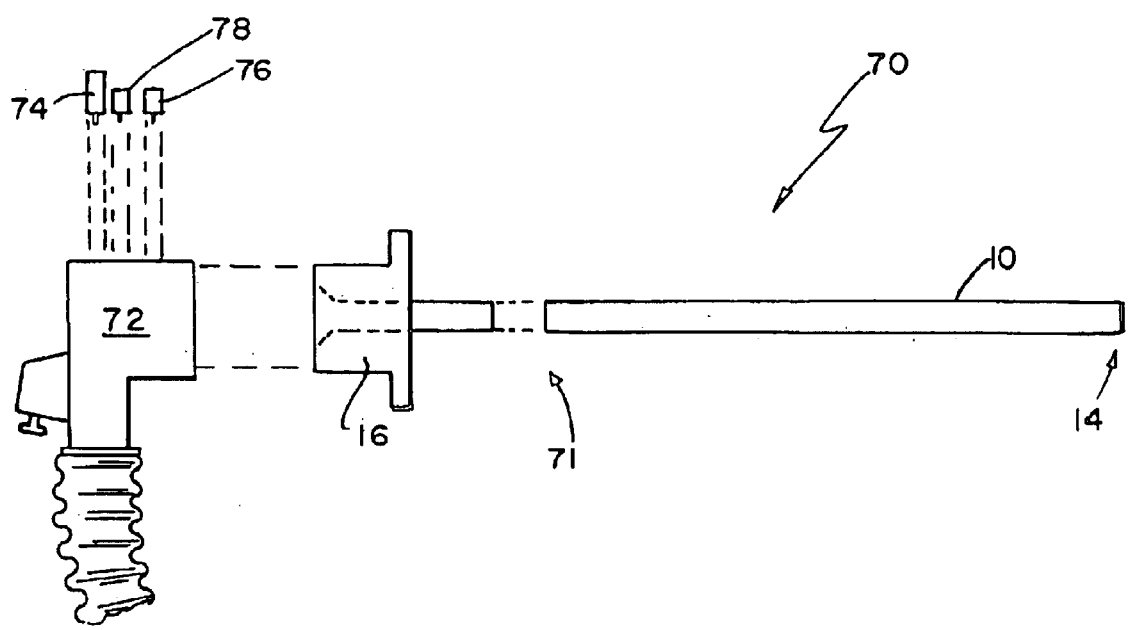
FIG. 11 is a diagrammatical view of another embodiment of the apparatus of the present invention for detecting the location of a distal end of a tube within a body conduit.

FIG. 11 illustrates another embodiment of the apparatus 70 for acoustically guiding and monitoring the position of an ETT 10 within a body. As shown in this embodiment, speaker 74 and microphones 76, 78 can be alternatively coupled to ventilator 72 rather than connector 16. Otherwise, the embodiment functions as disclosed above.

Figure 12:
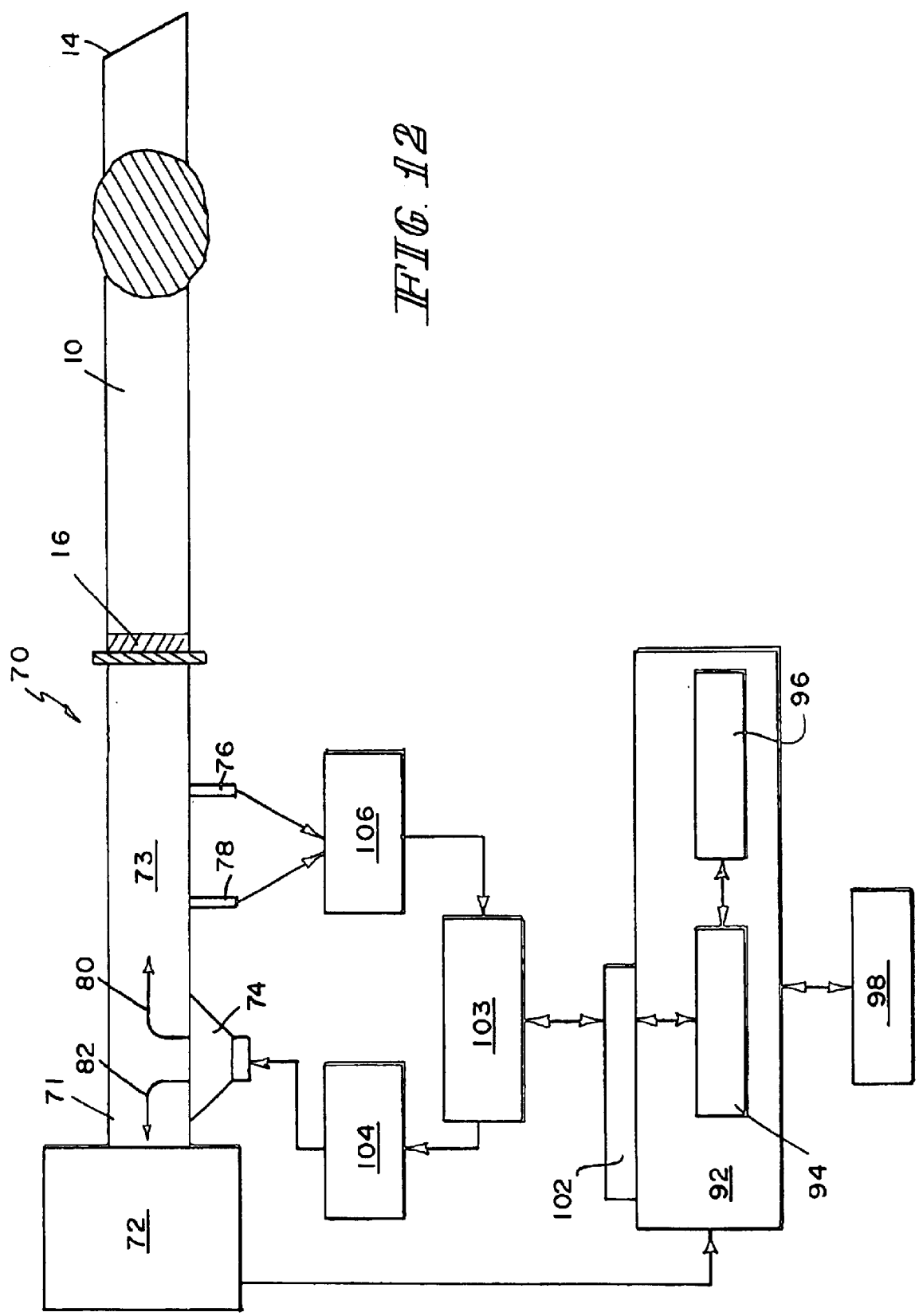
FIG. 12 is a diagrammatical view of another embodiment of the apparatus of the present invention for detecting the location of a distal end of a tube within a body conduit showing the use of a processor.

FIG. 12 illustrates yet another embodiment of the apparatus 70 for acoustically guiding and monitoring the position of a tube 10 within a body conduit, showing the use of a computer 92 in the place of the discriminator 110 and position indicator 112 of FIG. 9. Apparatus 70 includes tube 10 which is defined by a distal end 14 and a proximal end 71, the proximal end 71 being communicatively coupled to any type of medical device (i.e. a mechanical ventilator) 72 that is capable of cooperating with the apparatus 70. Apparatus 70 further includes a connector 16 that connects tube 10 with conduit 73, and a speaker 74 coupled to the conduit 73. In the preferred embodiment, a first microphone 76 is coupled to conduit 73 at a distal position relative to speaker 74, and a second microphone 78 is positioned between speaker 74 and microphone 76.

In the embodiment shown in FIG. 12, computer 92 includes a central processing unit (CPU) 94 and an internal memory 96. Illustratively, computer 92 is a PC based computer including a 200 MHZ processor and display 98. Illustratively, computer 92 runs a customized, menu-driven program under a Windows format. It is understood, however, that computer 92 may be any microcontroller or microprocessor. In addition, although the illustrated embodiment is PC based, a hand-held unit containing a microprocessor or microcontroller along with an LCD display 98 may be used in accordance with the present invention.

Illustratively, speaker 74 is a driver model XL-9689 available from Knowles Electronics. Speaker 74 is located in an outer wall of conduit 73. Computer 92 is coupled to an input of a digital-to-analog (D/A) converter 102. Illustratively, converter 102 is a PCI-MIO-16E-1 model available from National Instruments. Converter 102 has an output coupled to an input of a BNC Connector 103. Connector 103 is coupled to amplifier 104. Illustratively, connector 103 is a BNC-2090 model available from National Instruments. An output of amplifier 104 is coupled to speaker 74, and outputs of microphones 76, 78 are coupled to amplifier 106. Illustratively, amplifiers 104, 106 are model PMA-920 available from Denon. Computer 92 therefore controls speaker 74 to generate sonic pulses in conduit 73. In air-filled tubes, sonic pulses may have durations ranging from 0.01 ms to 10.00 ms. In other embodiments, i.e. with liquid-filled tubes, the sonic pulse durations will vary depending on the characteristics of the medium.

Two pulses propagating in opposite directions emanate from speaker 74. The distally traveling incident pulse propagates down conduit 73 in the direction of arrow 80. The incident sound pulse also travels in the direction of arrow 82. The incident pulse traveling in the direction of arrow 80 is recorded as it first passes over the second microphone 78, then the first microphone 76, and continues to propagate down and out of distal end 14 of ETT 10. Reflections of this incident pulse occur from within the airways and travel back toward the proximal end 71 of conduit 73, to be recorded first by first microphone 76 and second by second microphone 78. The analog outputs of microphones 76, 78 are digitized by A/D converter 102. The digital representations are then stored for analysis in memory 96 of computer 92.

Microphones 76, 78 cooperate with computer 92 to provide a directionally sensitive reading of a sound pulse as it propagates past the set of microphones 76, 78 in the following manner. In the instance where a sound pulse is recorded by first microphone 76 before it is recorded by second microphone 78, computer 92 determines that the sound pulse is traveling from the distal end 14 of the tube 10 to the proximal end 71. If, on the other hand, the sound pulse is first recorded by second microphone 78, and later by first microphone 76, the sound pulse is determined to be traveling toward the distal end 14 of the tube 10 originating from either speaker 74 as an incident sound pulse, or as a reflection from the proximal end 71. Sound pulses that are determined to be reflections from proximal end 71 can be disregarded by computer 92, since these pulses do not need to be analyzed for tube placement. Differentiation can be made between incident sound pulses and reflected sound pulses by considering the distance between the speaker 74 and microphones 76, 78, and the time elapsed since the initiation of the sound pulse, as discussed above.

Figure 13:
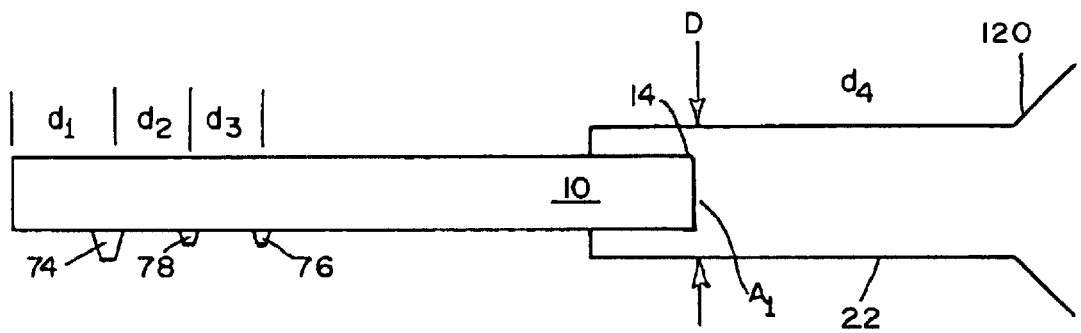
FIG. 13 is a diagrammatical view of the apparatus of FIG. 12, showing the insertion of the apparatus in a trachea and the distances that are relevant during the insertion thereof.

As shown in FIG. 13, the preferred embodiment of the invention uses an acoustic method to accurately measure three parameters within the body system. The first parameter is the distance $d_4$, which will be referred to as insertion depth. The physical meaning of this distance is the separation between the distal end 14 of the ETT 10 and the point 120 in the airways where a sudden increase in cross-sectional area occurs. The knowledge of this distance would allow a clinician to properly position the ETT 10 within the trachea 22. The second parameter is the diameter D of the trachea 22 at its interface with the ETT 10. According to the invention, the measurement of this parameter will allow the distinction between tracheal, bronchial, and esophageal intubation. The third and final parameter is the location and magnitude of any obstructions present in the (ETT) tube 10. This measure will allow the health care provider to constantly assess the patency of the ETT.

By providing two microphones, the present invention can determine the direction of travel of a sound pulse, and thereby eliminate the need to have a sound pulse absorber at the proximal end of the microphone that minimizes reflections from the proximal end. Furthermore, because a sound pulse absorber is not needed, a valve mechanism for routing the sound pulse to the absorber is not required by the invention.

In yet another embodiment of the present invention, the two-microphone system can be replaced by a single microphone (or single pulse-receiving) system, provided the single microphone allows directional discrimination of the sound pulse. For example, if a system is provided that includes only a single microphone that is directionally sensitive, the same directionally discriminating effect can be accomplished.

It is advantageous for the time delay between the microphones to be an integer multiple of the sampling period used to digitize the reflected waveforms, or $$t_d = mt_s \qquad (6)$$

where m is an integer.

The time delay between microphones 76, 78 can be determined in the following manner:

Microphones 76, 78 are mounted in tube 10 at a preselected distance $d_3$ of, for example, 5 cm apart from each other. Speaker 74 is placed a distance $d_2$, for example 2 cm, from second microphone 78. Actual distances are preferably much shorter, and these distances were selected only for trial purposes.

A sound pulse is thereafter generated by speaker 74 and recorded by microphones 78 at a suitable sampling rate. The use of this high sampling frequency improves the time resolution of the reflected waveform and allows for a more accurate determination of the time delay between the microphones. The time delay is calculated which also implies a sound propagation speed. A value of m is chosen to determine the sampling period required via equation (6).

At least three pieces of information can be extracted from the acoustic data that are important for the development of a guidance and monitoring system. These are the distance $d_4$ between the distal end 14 of tube 10 and the acoustical end of the airways 22, the diameter D of the trachea or body cavity just after the distal end 14 of the tube 10, and the location and magnitude of obstructions present in tube 10. The determination of each of these parameters requires the application of several algorithms which are based on the principles of sound propagation in tubes.

Figure 14:
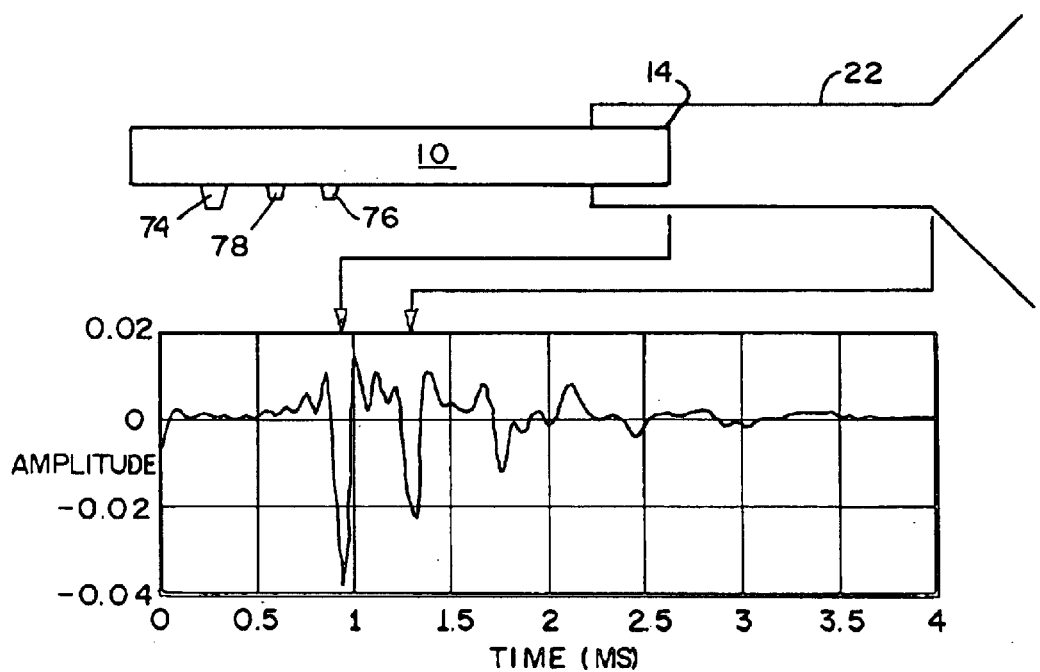
FIG. 14 is a graphical representation of the relationship between the geometry of a tube and the acoustic reflections recorded by the apparatus of the present invention.

The determination of the insertion depth $d_4$ is based on the principle that for plane wave propagation, a reflection will occur wherever there is a change in cross-sectional area. FIG. 14 shows how peaks in the acoustic response correspond to changes in cross-sectional area. The first peak, which occurs at approximately 0.95 ms, is due to the change in cross-sectional area at the boundary between the tube 10 and the trachea 22. The second peak (1.3 ms) corresponds to the sudden increase in cross-sectional area that occurs in the airways. The distance calculated is derived from time delay between Incident pulse and airway reflection (provides distance estimate between microphone and airway region). Therefore, the distance $d_4$ can be calculated by measuring the time delay between the incident pulse peak and the airway reflected pulse peak, and thereafter substituting the delay in the following equation.

$$d_4 = \frac{ct_d}{2} \qquad (7)$$

The diameter of the trachea 22 can be estimated from the system acoustic response by measuring the reflection coefficient at the boundary between both the ETT tube 10 and the trachea 22. In cases where the endotracheal tube 10 fits snugly inside a trachea 22, the diameter of the trachea can be determined by the following equation:

$$D = \sqrt{\frac{1-R}{1+R}} \cdot D_1 \qquad (8)$$

In the event that the outer diameter of the ETT 10 is smaller than the trachea 22, the diameter of the trachea can be estimated by the following equation:

$$D = \sqrt{\frac{(1-R)D_1^2 - (1+R)D_2^2}{2(1+R)}} \qquad (9)$$

Figure 15:
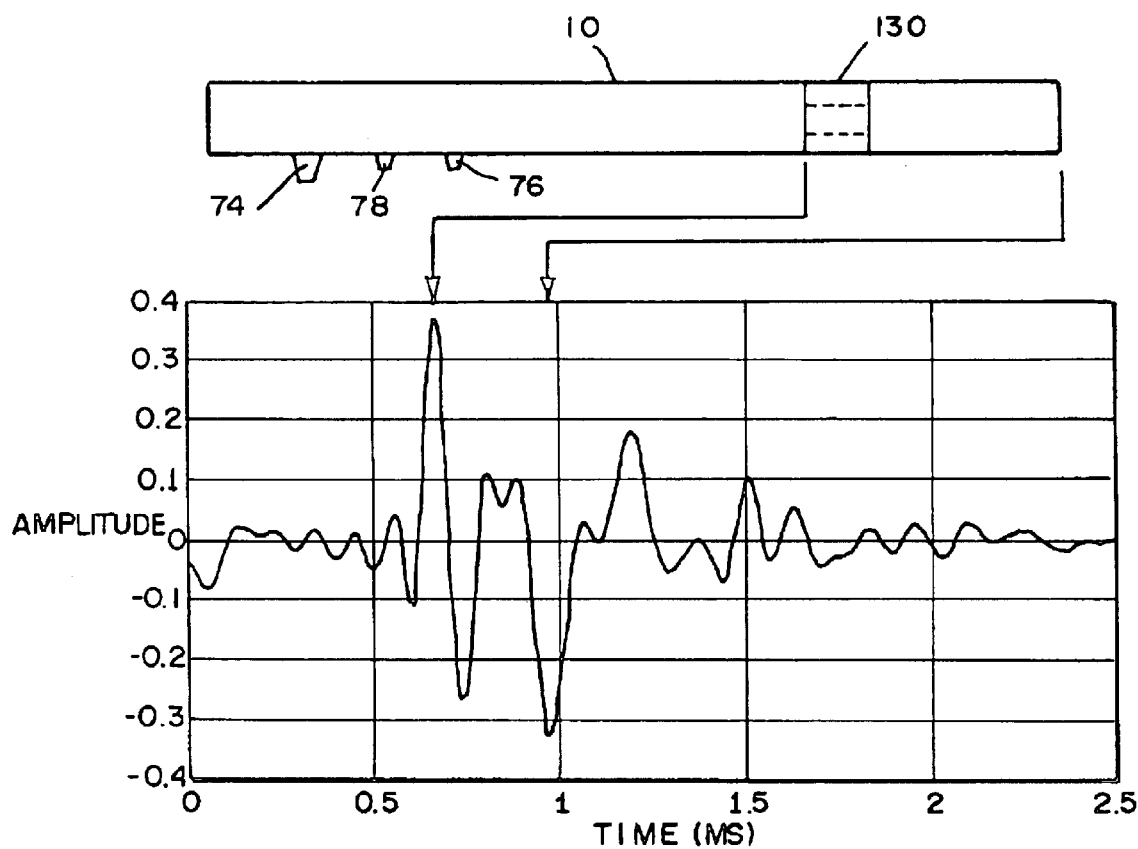
FIG. 15 is a graphical representation of the acoustic reflections recorded by the apparatus of the present invention when an obstruction is present in the tube.

As shown in FIG. 15, if an obstruction 130 occurs within the ETT 10, an acoustic reflection will occur at that point due to a change in cross-sectional area. The degree of the lumen constriction can be estimated by measuring the reflection coefficient at the point of the obstruction. The method used to calculate the reflection coefficient is similar to the one used to estimate the diameter of the trachea 22. Once the reflection coefficient is estimated, the percent lumen constriction can be found using:

$$\%LC = \left(1 - \frac{1-R}{1+R}\right) * 100\% \qquad (10)$$

This additional capability of detecting the buildup of mucus or fluid inside the ETT can indicate when an ETT requires suctioning. Any significant mucous buildup along the inner walls of the ETT would alter the constant ETT cross-sectional area and is detected by examining the reflections, if any, that precede in time the tube tip reflection. Using these reflections, the locations and amounts of excess mucus along the inner ETT walls are then estimated using equations (5) and (7).

The invention can further include a warning signal generator, for signaling to an operator when an ETT may require suctioning, or when the airway diameter at the tip of the ETT is smaller than the outer diameter of the ETT. In other embodiments, the warning signal generator can be programmed to signal when any one of a number of preselected conditions is present, including non-desirable conditions at the tip of the tube, non-patency of the tube, and kinking of the tube.

Figure 16:
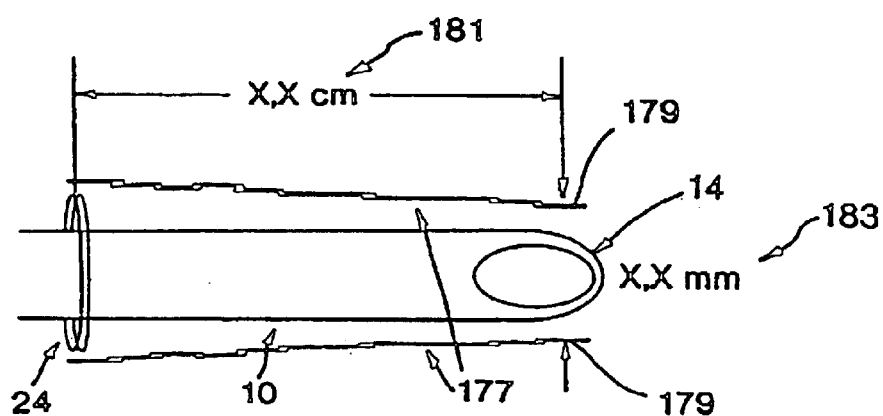
FIG. 16 is a diagrammatical view illustrating a visual display of the apparatus to provide visual indication to the user of the distance of insertion and of the estimated diameter of a body conduit into which the ETT is inserted.

After the estimated insertion distance and estimated airway diameter have been calculated by the system, they can be presented to the user in the convenient graphical format depicted in FIG. 16. This display consists of pictorial representation of ETT 10, a marker of the estimated position of vocal folds 24 in relation to the ETT tip, and boundary markers on either side of the ETT tip representing the estimated diameter of the airway at the tube tip. All movements of ETT 10 within the airway are reflected on the system display. Also, all previously estimated airway diameter markers 177 remain displayed at their corresponding position along ETT 10 which provides the user with a rough outline of the airway dimensions between the vocal folds 24 and the tube tip.

The invention may also be described as a method of acoustically detecting the relative location of a distal end of a tube within a body conduit. According to the this embodiment of the invention, an incident sound pulse is generated in the tube, a reflected sound pulse is detected, the direction of travel of the reflected sound pulse is determined, and the position of the tube relative to the body conduit is determined. The invention may also include the step of determining whether the tube is obstructed. The invention may further include the step of generating a warning signal upon the occurrence of preselected conditions. The position determining step may include the step of estimating the dimensions of the body conduit adjacent the distal end of the tube, as disclosed above. Furthermore, the position determining step may include the step of comparing a first signal representing a sound pulse detected by a first microphone with a second signal representing a sound pulse detected by a second microphone.

The general method required to employ acoustical guidance according to the apparatus and method of the present invention requires certain specific steps to be followed. First, the acoustical properties of the medium in which the sound pulses will be propagated must be analyzed and determined. For example, sound speed and acoustic losses in the medium such as blood, air, or urine must be determined. The next step of the method is to determine the acoustic wall properties of the body conduit in which the tube or catheter will reside. Properties such as compliance, mass, and resistance must be determined for the conduit or cavity into which the tube or catheter is inserted. Next, anatomical boundaries that give rise to specific identifiable reflections must be determined. For instance, a pulse may be reflected off a valve between the bladder and urethra when inserting a tube or catheter into the bladder. Next, amplitude requirements for exogeneous sound pulses to be delivered to ensure detectable reflections from the key boundaries must be determined. The operator must also determine pulse width and shape (and therefore frequency content) to optimize reflections from boundaries of interest to allow calculations of distances, dimensions, etc. to be made. Finally, particular sound generators such as speakers, detectors such as microphones, connectors, and valves must be coupled together to propagate sound forces into a body, detect reflected pulses, and process the detected pulses.

Although the method and apparatus described is related to guiding and positioning an ETT 10 within a respiratory system of a body, it is understood that the apparatus and method of the present invention may be used to guide insertion of gas or liquid filled tubes or catheters into other body cavities or in various mechanical operations. The acoustical guidance apparatus and method can be applied to a wide variety of clinical tubes or catheters where accurate placement and position monitoring is required. For example, the apparatus and method can be used to ensure proper feeding tube placement in the stomach and not in the esophagus or small intestine. The apparatus and method can be used to determine the location of a urinary catheter for diagnosis and relief of incontinence or for other reasons. The apparatus and method can also be used to position arterial and venous catheters to measure physiological parameters and deliver therapeutic pharmaceuticals. Also illustratively, the apparatus and method can be used to monitor the position of indwelling heart catheters used in hemodynamic clinical studies.

Although the invention has been described in detail with reference to a certain preferred embodiment, variations and modifications exist within the scope and spirit of the invention as described and defined in the following claims.

We claim:

1. An apparatus for acoustically detecting the location of a distal end of a tube relative to a body conduit into which the tube is being inserted, the tube having a proximal end and a distal end, the distal end formed for insertion into the body conduit, the apparatus comprising:

a speaker positioned to generate a sound pulse in the tube;
   a first microphone for detecting a sound pulse in the tube at a distal position relative to the speaker, and for generating a first signal corresponding to the detected sound pulse;
   a second microphone for detecting a sound pulse at a position in the tube between the first microphone and the speaker, and for generating a second signal corresponding to a detected sound pulse; and
   a processor configured to receive the first and second signals and to discriminate between a distally traveling sound pulse and a proximally traveling sound pulse as the distal end of the tube is moved relative to the body conduit, the processor using the first or second signal generated from detection of the proximally traveling sound pulse to determine and report the location of the distal end of the tube relative to the body conduit.

2. The apparatus of claim 1, wherein the tube is adapted to be coupled to a medical device.

3. The apparatus of claim 2, wherein the medical device is one selected from the group consisting of a mechanical ventilator, a breathing bag, an anesthesia machine, and an infusion pump.

4. An apparatus for acoustically detecting the location of a distal end of a tube relative to a body conduit into which the tube is being inserted, the tube having a proximal end and a distal end, the distal end formed for insertion into the body conduit, the apparatus comprising:

a speaker for generating a sound pulse in the tube;
   a first microphone for detecting a sound pulse in the tube at a distal position relative to the speaker, and for generating a first signal corresponding to the detected sound pulse;

a second microphone for detecting a sound pulse at a position in the tube between the first microphone and the speaker, and for generating a second signal corresponding to a detected sound pulse; and a processor configured to receive the first and second signals and to discriminate between a distally traveling sound pulse and a proximally traveling sound pulse as the distal end of the tube is moved relative to the body conduit, the processor using the first or second signal generated from detection of the proximally traveling sound pulse to determine and report the location of the distal end of the tube relative to the body conduit, wherein the processor is further configured to detect a blockage in the tube.

5. The apparatus of claim 4, wherein the blockage is total.

6. The apparatus of claim 4, wherein the blockage is partial.

7. An apparatus for acoustically detecting the location of a distal end of a tube relative to a body conduit into which the tube is being inserted, the tube having a proximal end and a distal end, the distal end formed for insertion into the body conduit, the apparatus comprising:

a speaker for generating a sound pulse in the tube;

a first microphone for detecting a sound pulse in the tube at a distal position relative to the speaker, and for generating a first signal corresponding to the detected sound pulse;

a second microphone for detecting a sound pulse at a position in the tube between the first microphone and the speaker, and for generating a second signal corresponding to a detected sound pulse; and a processor configured to receive the first and second signals and to discriminate between a distally traveling sound pulse and a proximally traveling sound pulse as the distal end of the tube is moved relative to the body conduit, the processor using the first or second signal generated from detection of the proximally traveling sound pulse to determine and report the location of the distal end of the tube relative to the body conduit, wherein the processor is further configured to detect a kink in the tube.

8. An apparatus for acoustically detecting the location of a distal end of a tube relative to a body conduit into which the tube is being inserted, the tube having a proximal end and a distal end, the distal end formed for insertion into the body conduit, the apparatus comprising:

a speaker for generating a sound pulse in the tube;

a first microphone for detecting a sound pulse in the tube at a distal position relative to the speaker, and for generating a first signal corresponding to the detected sound pulse;

a second microphone for detecting a sound pulse at a position in the tube between the first microphone and the speaker, and for generating a second signal corresponding to a detected sound pulse; and a processor configured to receive the first and second signals and to discriminate between a distally traveling sound pulse and a proximally traveling sound pulse as the distal end of the tube is moved relative to the body conduit, the processor using the first or second signal generated from detection of the proximally traveling sound pulse to determine and report the location of the distal end of the tube relative to the body conduit, wherein the processor provides a signal representing the dimensions of the body conduit adjacent the distal end of the tube.

9. The apparatus of claim 8, further comprising a warning signal generator for signaling when the dimensions signaled by the processor are not within a predetermined range.

10. An apparatus for acoustically detecting the location of a distal end of a tube relative to a body conduit into which the tube is being inserted, the tube having a proximal end and a distal end, the distal end formed for insertion into the body conduit, the apparatus comprising:

a speaker for generating a sound pulse in the tube;

a first microphone for detecting a sound pulse in the tube at a distal position relative to the speaker, and for generating a first signal corresponding to the detected sound pulse;

a second microphone for detecting a sound pulse at a position in the tube between the first microphone and the speaker, and for generating a second signal corresponding to a detected sound pulse; and a processor configured to receive the first and second signals and to discriminate between a distally traveling sound pulse and a proximally traveling sound pulse as the distal end of the tube is moved relative to the body conduit, the processor using the first or second signal generated from detection of the proximally traveling sound pulse to determine and report the location of the distal end of the tube relative to the body conduit, further comprising a warning signal generator for signaling when the distal end of the tube moves relative to the body conduit.

11. An apparatus for acoustically detecting the location of a distal end of a tube relative to a body conduit into which the tube is being inserted, the tube having a proximal end and a distal end, the distal end formed for insertion into the body conduit, the apparatus comprising:

a speaker for generating a sound pulse in the tube;

a first microphone for detecting a sound pulse in the tube at a distal position relative to the speaker, and for generating a first signal corresponding to the detected sound pulse;

a second microphone for detecting a sound pulse at a position in the tube between the first microphone and the speaker, and for generating a second signal corresponding to a detected sound pulse; and a processor configured to receive the first and second signals and to discriminate between a distally traveling sound pulse and a proximally traveling sound pulse as the distal end of the tube is moved relative to the body conduit, the processor using the first or second signal generated from detection of the proximally traveling sound pulse to determine and report the location of the distal end of the tube relative to the body conduit, further comprising a display in electronic communication with the processor.

12. The apparatus of claim 11, wherein the display provides an indication of the dimensions of the body conduit adjacent the distal end of the tube.

13. The apparatus of claim 11, wherein the display provides an indication of the patency of the tube.

14. The apparatus of claim 11, wherein the display provides an indication of the location of the distal end of the tube relative to the body conduit.

15. An apparatus for acoustically detecting the:location of a distal end of a tube relative to a body into which the tube is inserted, the tube having a proximal end and a distal end, the distal end formed for insertion into the body conduit, the apparatus comprising:

a sound pulse generator positioned to generate a sound in the tube;

a sound pulse receiver for signaling the detection of a sound pulse; a position indicator configured to report the location of the distal end of the tube relative to the body during insertion of the distal end of the tube into the body using the signal from the sound pulse receiver; and means for discriminating between a sound pulse traveling away from the distal end of the tube and a sound pulse traveling toward the distal end of the tube.

16. The apparatus of claim 15, wherein the sound pulse receiver comprises a first microphone and a second microphone.

17. The apparatus of claim 15, wherein the sound pulse receiver comprises a directionally sensitive microphone.

18. The apparatus of claim 15, wherein the sound pulse receiver is located at a distal position relative to the sound pulse generator.

19. The apparatus of claim 15, wherein the sound pulse receiver is located at a proximal position relative to the sound pulse generator.

20. The apparatus of claim 15, further comprising a medical device coupled to the tube.

21. An apparatus for acoustically detecting the location of a distal end of a tube relative to a body into which the tube is inserted, the tube having a proximal end and a distal end, the distal end formed for insertion into the body conduit, the apparatus comprising:

a sound pulse generator;

a sound pulse receiver for signaling the detection of a sound pulse; a position indicator configured to report the location of the distal end of the tube relative to the body during insertion of the distal end of the tube into the body using the signal from the sound pulse receiver; and means for discriminating between a sound pulse traveling away from the distal end of the tube and a sound pulse traveling toward the distal end of the tube, wherein the position indicator determines whether the tube is obstructed.

22. An apparatus for acoustically detecting the location of a distal end of a tube relative to a body into which the tube is inserted, the tube having a proximal end and a distal end, the distal end formed for insertion into the body conduit, the apparatus comprising:

a sound pulse generator;

a sound pulse receiver for signaling the detection of a sound pulse; a position indicator configured to report the location of the distal end of the tube relative to the body during insertion of the distal end of the tube into the body using the signal from the sound pulse receiver; and means for discriminating between a sound pulse traveling away from the distal end of the tube and a sound pulse traveling toward the distal end of the tube, wherein the position indicator estimates dimensions of the body adjacent the distal end of the tube.

23. The apparatus of claim 22, further comprising a warning signal generator for signaling when the dimensions estimated by the position indicator are not within a predetermined range.

24. An apparatus for acoustically detecting the location of a distal end of a tube relative to a body into which the tube is inserted, the tube having a proximal end and a distal end, the distal end formed for insertion into the body conduit, the apparatus comprising:

a sound pulse generator;

a sound pulse receiver for signaling the detection of a sound pulse; a position indicator configured to report the location of the distal end of the tube relative to the body during insertion of the distal end of the tube into the body using the signal from the sound pulse receiver; and means for discriminating between a sound pulse traveling away from the distal end of the tube and a sound pulse traveling toward the distal end of the tube, An apparatus further comprising a warning signal generator for signaling when the distal end of the tube moves relative to the body.

25. An apparatus for acoustically detecting the location of a distal end of a tube relative to a body into which the tube is inserted, the tube having a proximal end and a distal end, the distal end formed for insertion into the body conduit, the apparatus comprising:

a sound pulse generator;

a sound pulse receiver for signaling the detection of a sound pulse; a position indicator configured to report the location of the distal end of the tube relative to the body during insertion of the distal end of the tube into the body using the signal from the sound pulse receiver; and means for discriminating between a sound pulse traveling away from the distal end of the tube and a sound pulse traveling toward the distal end of the tube, further comprising a display in electronic communication with the position indicator.

26. A method of acoustically detecting the location of a distal end of a tube relative to a body, comprising the steps of:

generating a sound pulse in the tube;

detecting a sound pulse;

determining the direction of travel of the detected sound pulse;

determining the position of the distal end of the tube relative to the body using a detected sound pulse determined to be traveling away from the distal end of the tube; and determining whether the tube should be moved relative to the body based upon the determined position of the distal end of the tube.

27. A method of acoustically detecting the location of a distal end of a tube relative to a body, comprising the steps of:

generating a sound pulse in the tube;

detecting a sound pulse;

determining the direction of travel of the detected sound pulse;

determining the position of the distal end of the tube relative to the body using a detected sound pulse determined to be traveling away from the distal end of the tube; and determining whether the tube should be moved relative to the body based upon the determined position of the distal end of the tube, further comprising the step of determining whether the tube is obstructed.

28. A method of acoustically detecting the location of a distal end of a tube relative to a body comprising the steps of:

generating a sound pulse in the tube;

detecting a sound pulse;

determining the direction of travel of the detected sound pulse;

determining the position of the distal end of the tube relative to the body using a detected sound pulse determined to be traveling away from the distal end of the tube; and determining whether the tube should be moved relative to the body based upon the determined position of the distal end of the tube, further comprising the step of determining whether the tube is kinked.

29. A method of acoustically detecting the location of a distal end of a tube relative to a body, comprising the steps of:

generating a sound pulse in the tube;

detecting a sound pulse;

determining the direction of travel of the detected sound pulse;

determining the position of the distal end of the tube relative to the body using a detected sound pulse determined to be traveling away from the distal end of the tube; and determining whether the tube should be moved relative to the body based upon the determined position of the distal end of the tube, wherein the position determining step includes estimating the dimensions of the body adjacent the distal end of the tube.

30. The method of claim 29, further comprising the step of generating a warning signal when the estimated dimensions are not within a predetermined range.

31. A method of acoustically detecting the location of a distal end of a tube relative to a body, comprising the steps of:

generating a sound pulse in the tube;

detecting a sound pulse;

determining the direction of travel of the detected sound pulse;

determining the position of the distal end of the tube relative to the body using a detected sound pulse determined to be traveling away from the distal end of the tube; and determining whether the tube should be moved relative to the body based upon the determined position of the distal end of the tube, further comprising the step of generating a warning signal when the distal end of the tube moves relative to the body.

32. A method of acoustically detecting the location of a distal end of a tube relative to a body, comprising the steps of:

generating a sound pulse in the tube; detecting a sound pulse;

determining the direction of travel of the detected sound pulse;

determining the position of the distal end of the tube relative to the body using a detected sound pulse determined to be traveling away from the distal end of the tube; and determining whether the tube should be moved relative to the body based upon the determined position of the distal end of the tube, wherein the position determining step includes the step of comparing a first signal representing a sound pulse detected by a first microphone with a second signal representing a sound pulse detected by a second microphone.

* * * * *